United States Patent
Tatsuda (10) Patent No.: US 9,983,120 B2
(45) Date of Patent: May 29, 2018

(54) COLORIMETRY METHOD AND COLORIMETRY APPARATUS

(71) Applicant: SEIKO EPSON CORPORATION, Tokyo (JP)

(72) Inventor: Tetsuo Tatsuda, Ina (JP)

(73) Assignee: SEIKO EPSON CORPORATION, Tokyo (JP)

( * ) Notice: Subject to any disclaimer, the term of this patent is extended or adjusted under 35 U.S.C. 154(b) by 354 days.

(21) Appl. No.: 14/169,923

(22) Filed: Jan. 31, 2014

(65) Prior Publication Data

US 2014/0218735 A1  Aug. 7, 2014

(30) Foreign Application Priority Data

Feb. 5, 2013  (JP) ................................ 2013-020167

(51) Int. Cl.
   *G01N 21/25* (2006.01)
   *G01J 3/28* (2006.01)
   (Continued)

(52) U.S. Cl.
   CPC .......... *G01N 21/251* (2013.01); *G01J 3/0208* (2013.01); *G01J 3/0262* (2013.01);
   (Continued)

(58) Field of Classification Search
   CPC ...... G01J 3/0264; G01J 3/0272; G01J 3/1256; G01J 3/2823; G01J 3/51; G01J 2003/2826; G01N 21/251
   See application file for complete search history.

(56) References Cited

U.S. PATENT DOCUMENTS

| 527,518 A | 10/1894 | Weaver |
| 6,335,984 B1 * | 1/2002 | Taguchi ................ G01J 3/02 356/318 |

(Continued)

FOREIGN PATENT DOCUMENTS

| CN | 1672021 A | 9/2005 |
| CN | 102735340 A | 10/2012 |

(Continued)

OTHER PUBLICATIONS

English translation of JP 2008151781, Jul. 3, 2008.*

*Primary Examiner* — Dominic J Bologna
(74) *Attorney, Agent, or Firm* — Oliff PLC (57) ABSTRACT

An imaging section that detects the amount of light separated by a wavelength tunable interference filter to acquire a spectroscopic image (imaging device and light amount acquisition section) detects the amount of light successively separated for three wavelengths to acquire spectroscopic images for producing a combined image. A display controller causes a display section to display a combined image based on the spectroscopic images for producing the combined image. A specified position detection section identifies based on user's operation a specified position where a colorimetry result is to be outputted. The imaging section detects the amount of light successively separated for a plurality of wavelengths by the wavelength tunable interference filter to acquire spectroscopic images for colorimetry corresponding to the plurality of wavelengths. A colorimetry section measures the color in the specified position by using the amount of light obtained from each of the spectroscopic images for colorimetry.

12 Claims, 8 Drawing Sheets

(51) Int. Cl.
*G01J 3/02* (2006.01)
*G01J 3/26* (2006.01)
*G01J 3/51* (2006.01)

(52) U.S. Cl.
CPC ........... *G01J 3/0264* (2013.01); *G01J 3/0272* (2013.01); *G01J 3/0283* (2013.01); *G01J 3/26* (2013.01); *G01J 3/2823* (2013.01); *G01J 3/51* (2013.01); *G01J 2003/2826* (2013.01)

(56) References Cited

U.S. PATENT DOCUMENTS

| | | | | |
|---|---|---|---|---|
| 6,353,673 | B1* | 3/2002 | Shnitser | G06K 9/3241 |
| | | | | 382/103 |
| 7,262,779 | B1* | 8/2007 | Sones | G01J 3/02 |
| | | | | 345/589 |
| 2006/0152586 | A1 | 7/2006 | Komiya et al. | |
| 2006/0181543 | A1* | 8/2006 | Katsumata | G01J 3/28 |
| | | | | 345/589 |
| 2007/0153287 | A1* | 7/2007 | Lin | G01J 3/02 |
| | | | | 356/454 |
| 2008/0080027 | A1 | 4/2008 | Mestha et al. | |
| 2008/0192235 | A1 | 8/2008 | Komiya et al. | |
| 2008/0266563 | A1* | 10/2008 | Redman | G01J 3/02 |
| | | | | 356/406 |
| 2009/0067695 | A1 | 3/2009 | Komiya et al. | |
| 2012/0127471 | A1 | 5/2012 | Urushidani | |
| 2012/0300208 | A1* | 11/2012 | Sano | G01J 1/04 |
| | | | | 356/402 |
| 2016/0077260 | A1 | 3/2016 | Urushidani | |

FOREIGN PATENT DOCUMENTS

| | | |
|---|---|---|
| JP | H04-276526 A | 10/1992 |
| JP | H05-223642 A | 8/1993 |
| JP | B2-2713838 | 2/1998 |
| JP | A-2002-048719 | 2/2002 |
| JP | 2003-004533 A | 1/2003 |
| JP | A-2003-014546 | 1/2003 |
| JP | 2006-030014 A | 2/2006 |
| JP | A-2008-151781 | 7/2008 |
| JP | 2012-108440 | 6/2012 |

* cited by examiner

COLORIMETRY METHOD AND COLORIMETRY APPARATUS

BACKGROUND

1. Technical Field

The present invention relates to a colorimetry method and a colorimetry apparatus.

2. Related Art

There is a known technology of related art for measuring the color of an object under colorimetry, such as an image displayed on an image display apparatus and printed matter, to acquire a colorimetry result.

For example, there are a known image display apparatus and image display method that operate as follows: A multiband camera is used to image an object under colorimetry to acquire multiband images formed of band images corresponding to a plurality of bands (spectroscopic images for colorimetry); the multiband images are stored in a storage device, such as a hard disk drive; one of the acquired spectroscopic images for colorimetry is displayed on a screen; and each of the spectroscopic images for colorimetry is used to calculate the spectrum thereof in a position selected by a user on the displayed image and the calculated spectrum is displayed (JP-A-2008-151781).

In the technology described in JP-A-2008-151781, after a spectroscopic image stored in the storage device in advance is displayed on the screen, the spectrum in the position selected by the user is calculated. A spectroscopic image produced by capturing an image including a position where the user actually desires to acquire a spectrum therefore needs to be stored in the storage device in advance.

On the other hand, when a position where the user desires to perform colorimetry has not been determined, for example, when an object under colorimetry is an arbitrary object, no spectroscopic image for colorimetry, such as the stored image described above, has been stored in the storage device, and it is therefore necessary to acquire a plurality of spectroscopic images for colorimetry before the colorimetry is performed. In this case, it is preferable that images of an object under colorimetry are captured in real time and the user searches a position where the colorimetry is performed at the same time. To calculate an accurate spectrum, however, it is necessary to acquire a large number of spectroscopic images for colorimetry, for example, at 10-nm intervals over an entire possible region that may undergo the spectrum calculation. In view of the fact described above, when the apparatus described in JP-A-2008-151781 is used to acquire spectroscopic images for colorimetry in real time, spectroscopic images in positions that have not been selected as the position where colorimetry is performed are also undesirably acquired, resulting in inefficient colorimetry operation.

SUMMARY

An advantage of some aspects of the invention is to provide a colorimetry method and a colorimetry apparatus that allow efficient measurement of the color of an object under colorimetry.

An aspect of the invention is directed to a colorimetry method in a colorimetry apparatus including a spectroscopic filter capable of separating and selecting light of a predetermined wavelength from light incident from an object under colorimetry and changing the wavelength of the light to be selected, an imaging section that detects the amount of light of the wavelength selected by the spectroscopic filter to acquire a spectroscopic image, a display section that displays the image, a display controller that causes the display section to display a combined image that is a combination of spectroscopic images of at least three wavelengths acquired by the imaging section, a specified position detection section that detects a specified position specified by user's input operation in the combined image displayed on the display section, and a colorimetry section that measures the color of the object under colorimetry in the specified position based on the amount of light obtained in the specified position, the specified position formed of part of pixels of each of spectroscopic images for colorimetry corresponding to a plurality of wavelengths acquired by the imaging section, the method including causing the imaging section to detect the amount of light separated by the spectroscopic filter for the at least three wavelengths to acquire the spectroscopic images for producing the combined image, causing the display controller to display the combined image, which is the combination of the spectroscopic images for producing the combined image, on the display section, causing the specified position detection section to detect the specified position, causing the imaging section to detect the amount of light separated by the spectroscopic filter for a plurality of wavelengths to acquire the spectroscopic images for colorimetry, and causing the colorimetry section to measure the color in the specified position based on the spectroscopic images for colorimetry.

In the aspect of the invention, three wavelengths corresponding to R, G, and B colors are presented by way of example of the at least three wavelengths for which spectroscopic images for producing a combined image are acquired.

That is, one wavelength within each of the wavelength regions corresponding to R, G, and B is selected, and spectroscopic images of the selected three wavelengths are acquired. An image equivalent or similar to the object under colorimetry can thus be produced as a combined image that is the combination of the spectroscopic images.

In the aspect of the invention, to allow a user to specify a specified position where the user desires to perform colorimetry, the spectroscopic filter is used to separate light of each of the at least three wavelengths from incident light, the imaging section is used to acquire spectroscopic images of the at least three wavelengths for producing a combined image, and the display controller causes the display section to display the combined image, which is the combination of the spectroscopic images for producing a combined image. When the specified position detection section detects a specified position according to user's input operation, the spectroscopic filter is used to separate light of each of a plurality of wavelengths from the incident light, and the imaging section is used to acquire spectroscopic images of the plurality of wavelengths for colorimetry. The colorimetry section then performs colorimetry based on the amount of light in the specified position in each of the spectroscopic images.

Combining the spectroscopic images corresponding to the at least three wavelengths acquired to produce a combined image allows the display section to display the combined image (realtime image) equivalent or similar to the object under colorimetry. The user then selects a position while looking at the combined image displayed on the display section.

Therefore, only spectroscopic images for producing a combined image are acquired to select a specified position, and then spectroscopic images for colorimetry can be acquired only in a limited area containing a position where colorimetry is actually performed, whereby accurate colorimetry can be efficiently performed.

Further, since the user selects a specified position while looking at the combined image displayed on the display section, a desired position on the object under colorimetry can be appropriately and readily selected as the specified position, whereby a desired colorimetry result can be acquired.

In the colorimetry method according to the aspect of the invention, it is preferable that the step of acquiring the spectroscopic images for colorimetry is carried out after the step of detecting the specified position.

With this configuration, the step of acquiring the spectroscopic images for colorimetry is carried out after the step of detecting the specified position. As a result, an area corresponding to the specified position on the object under colorimetry can be identified, and an area over which spectroscopic images are acquired can be so limited that the area contains the area corresponding to the specified position on the object under colorimetry. Therefore, no spectroscopic image for colorimetry is acquired in an area where colorimetry is not performed but spectroscopic images for colorimetry can be acquired only in an area where colorimetry is performed, whereby accurate colorimetry can be efficiently measured.

In the colorimetry method according to the aspect of the invention, it is preferable that the step of acquiring the spectroscopic images for colorimetry is carried out for pixels contained in a portion specified as the specified position in the step of detecting the specified position.

With this configuration, an acquired spectroscopic image is an image formed of pixels contained in a portion specified as a specified position, that is, only a spectroscopic image for colorimetry in the specified position is acquired, whereby the color of an object under colorimetry can be more efficiently measured.

Another aspect of the invention is directed to a colorimetry apparatus including a spectroscopic filter capable of separating and selecting light of a predetermined wavelength from light incident from an object under colorimetry and changing the wavelength of the light to be selected, an imaging section that detects the amount of light of the wavelength selected by the spectroscopic filter to acquire a spectroscopic image, a display section that displays the image, a display controller that causes the display section to display a combined image that is a combination of spectroscopic images of at least three wavelengths acquired by the imaging section, a specified position detection section that detects a specified position specified by user's input operation in the combined image displayed on the display section, and a colorimetry section that measures the color of the object under colorimetry in the specified position based on the amount of light obtained in the specified position, the specified position formed of part of pixels of each of spectroscopic images for colorimetry corresponding to a plurality of wavelengths acquired by the imaging section.

In the aspect of the invention, spectroscopic images corresponding to at least three wavelengths acquired for producing a combined image are combined with one another, whereby a combined image equivalent or similar to the object under colorimetry can be displayed on the display section, as in the colorimetry method described above. Further, since the user selects a specified position while looking at the combined image displayed on the display section, a desired position on the object under colorimetry can be appropriately and readily selected as the specified position, whereby a desired colorimetry result can be acquired.

Moreover, since the user makes the selection while looking at the combined image, only spectroscopic images for producing a combined image are acquired to select a specified position, and then spectroscopic images for colorimetry can be acquired only in a limited area containing a position where colorimetry is actually performed, whereby accurate colorimetry can be efficiently performed.

In the colorimetry apparatus according to the aspect of the invention, it is preferable that the spectroscopic filter is a wavelength tunable Fabry-Perot etalon.

With this configuration, the spectroscopic filter is a wavelength tunable Fabry-Perot etalon capable of extracting light of a wavelength according to the dimension of the gap between a pair of reflection films.

A gap changer can therefore be driven to change the dimension of the gap to extract light of a plurality of wavelengths in a short period, whereby the time required for colorimetry can be reduced. Further, a Fabry-Perot etalon can be smaller, for example, than an AOTF (acousto-optic tunable filter) and an LCTF (liquid crystal tunable filter), whereby the size of the measurement apparatus can be reduced.

In the colorimetry apparatus according to the aspect of the invention, it is preferable that the specified position is a specified area containing a plurality of pixels, and the colorimetry section measures the color based on the average of the amounts of light obtained in the specified area in each of the spectroscopic images for colorimetry.

With this configuration, the specified position is a specified area containing a plurality of pixels of the imaging section, and a colorimetry result in the specified position is outputted based on the average of the amount of light obtained in the specified area. A colorimetry result in the specified area can thus be acquired. As a result, variation in the color of the object under colorimetry between dots (pixels) in the specified area and variation in light detection sensitivity between the pixels of the imaging section can be averaged, whereby the S/N ratio of a colorimetry result can be improved.

In the colorimetry apparatus according to the aspect of the invention, it is preferable that the colorimetry section measures the color at each pixel in each of the spectroscopic images for colorimetry.

With this configuration, colorimetry is performed on each pixel in a captured spectroscopic image. Therefore, even when the user changes a specified position to another, a colorimetry result can immediately be outputted.

It is preferable that the colorimetry apparatus according to the aspect of the invention further includes a light incident port through which the light incident from the object under colorimetry is introduced and a light blocker that is disposed around the light incident port and blocks external light other than the light incident from the object under colorimetry.

With this configuration, the light blocker is so disposed that it surrounds the introduction port of the colorimetry apparatus. The thus configured light blocker comes into contact with a surface of the object under colorimetry and can prevent external light other than the light from the object under colorimetry from entering the apparatus, whereby the colorimetry can be performed more accurately.

The light blacker preferably has an anti-reflective, light blocking surface. In this case, light will not be reflected off the surface, whereby no reflected light affects the colorimetry and no external light other than the light from the object under colorimetry will enter the apparatus.

BRIEF DESCRIPTION OF THE DRAWINGS

The invention will be described with reference to the accompanying drawings, wherein like numbers reference like elements.

DESCRIPTION OF EXEMPLARY EMBODIMENTS

Embodiment

Figure 1:
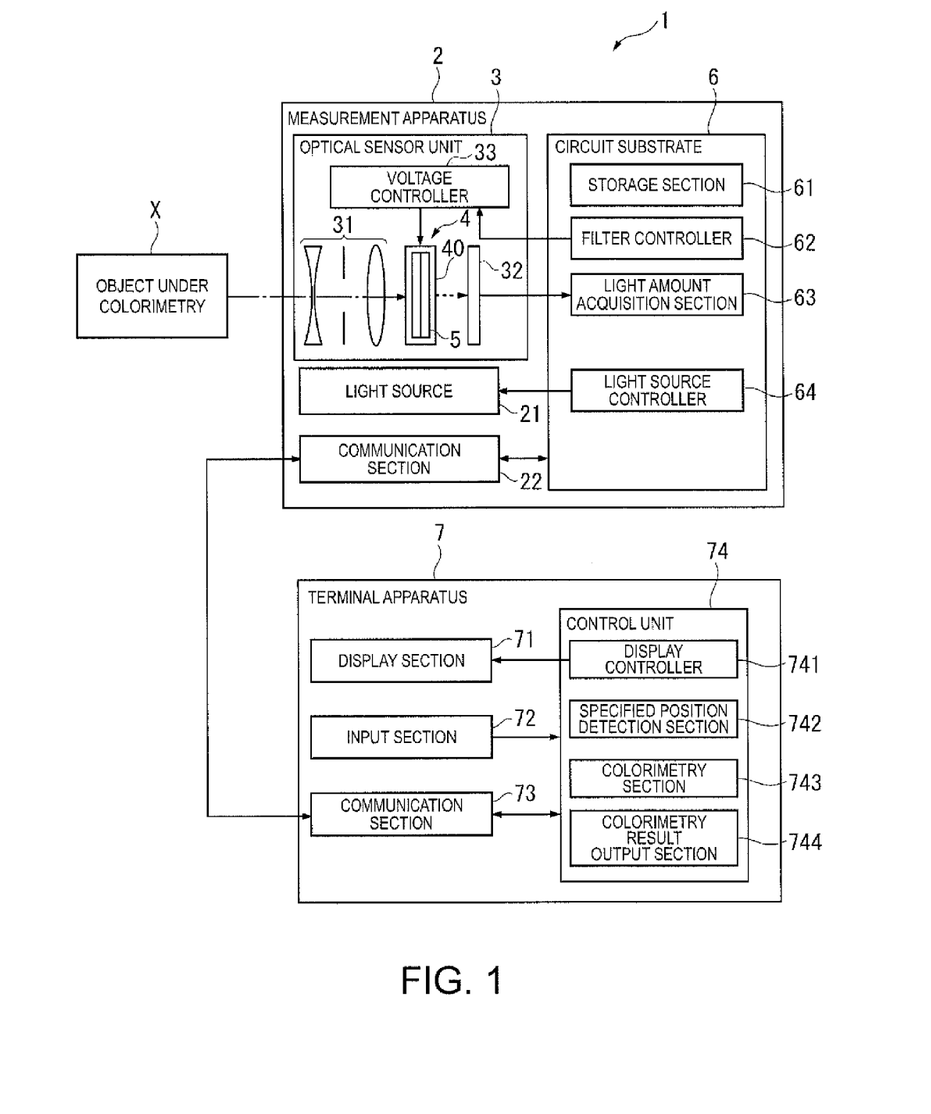
FIG. 1 is a block diagram showing a schematic configuration of a colorimetry system according to an embodiment of the invention.

An embodiment according to the invention will be described below with reference to the drawings.
Configuration of Colorimetry System FIG. 1 is a block diagram showing a schematic configuration of a colorimetry system 1 according to an embodiment of a colorimetry apparatus in which a colorimetry method according to an embodiment of the invention is implemented.

The colorimetry system 1 includes a measurement apparatus 2 and a terminal apparatus 7, which are so configured that they can communicate with each other, and corresponds to the colorimetry apparatus according to the embodiment of the invention.

The colorimetry system 1 measures light under measurement from an object X under colorimetry (incident light) and outputs a colorimetry result. The object X under colorimetry may, for example, be an image printed with a printer on a paper sheet or any other medium or an image displayed on a liquid crystal panel or any other display. The object X under colorimetry is not necessarily an image and may, for example, be a surface of an object. At this point, each realtime image that is a combination of spectroscopic images at three bands (three wavelengths) captured by the measurement apparatus 2 (combined image) is displayed on a display section 71 provided in the terminal apparatus 7. A user looks at the realtime images displayed on the display section 71 of the terminal apparatus 7 and specifies a position on the images, and the terminal apparatus 7 then detects the specified position. The measurement apparatus 2 then acquires a plurality of spectroscopic images based on the light under measurement, for example, at 10-nm wavelength intervals, performs color measurement (colorimetry) in the specified position on each of the spectroscopic images, and outputs a colorimetry result.

Configuration of Measurement Apparatus

Figure 2:
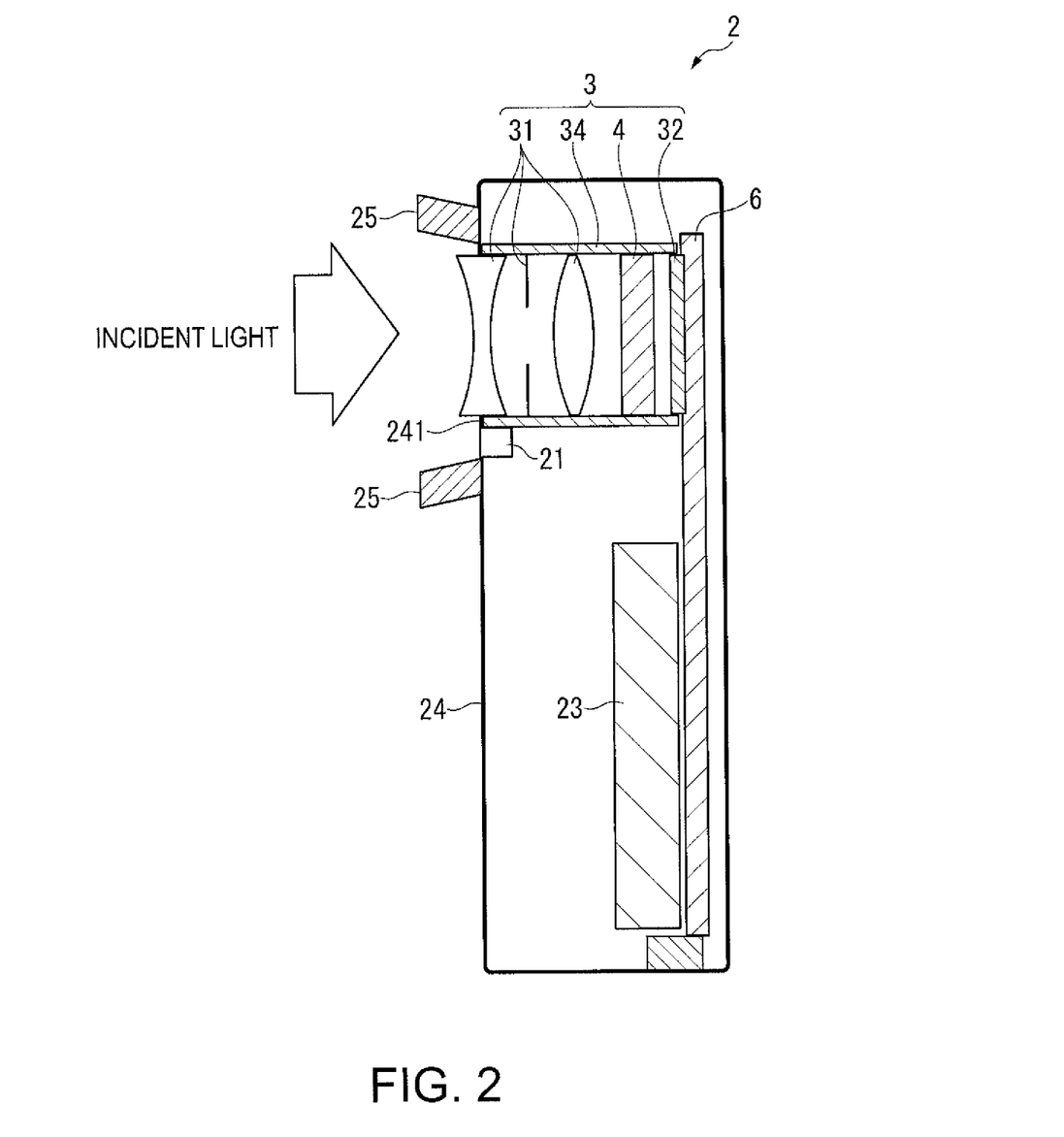
FIG. 2 is a cross-sectional view showing a schematic configuration of a measurement apparatus.

FIG. 2 is a cross-sectional view showing a schematic configuration of the measurement apparatus 2.

The measurement apparatus 2 includes an optical sensor unit 3, which captures the light under measurement from the object X under colorimetry, a circuit substrate 6, on which a variety of hardware components for controlling the measurement apparatus 2 (for example, CPU and other integrated circuits) are mounted, a light source 21, a communication section 22, and a battery 23, and the members described above are accommodated in an exterior case 24, as shown in FIGS. 1 and 2. The measurement apparatus 2 captures an image of the object X under colorimetry to acquire a spectroscopic image.

The exterior case 24 has a light incident port 241, through which the light under measurement is introduced to the optical sensor unit 3, and a tubular light blocker 25, which surrounds the light incident port 241 and protrudes from the exterior case 24. The light blocker 25, which is a light blocking member made of an elastic material, is pressed against a surface of the object X under colorimetry and then deforms and comes into intimate contact with the surface with no gap. The thus configured light blocker 25 prevents external light other than the light under measurement from entering the light incident port 241. The light blocker 25 has a black surface that can reduce the amount of light reflected off the surface.

The light source 21 is an LED or any other light source that emits white light and violet light and disposed in an area surrounded by the light blocker 25 but outside the light incident port 241 of the exterior case 24. The light source 21 emits the light toward the object X under colorimetry, and the measurement apparatus 2 measures light reflected off the object X under colorimetry.

The communication section 22 communicates with the terminal apparatus 7 and other external apparatus. The communication section 22 can communicate with them based on wired communication via a LAN or any other network and a variety of types of wireless communication, such as Wi-Fi (registered trademark), Bluetooth (registered trademark), and infrared communication.

The battery 23 is a power source that supplies the measurement apparatus 2 with electric power, specifically, a secondary battery chargeable via a charging circuit (not shown). The measurement apparatus 2 may instead be configured to be connectable to an external apparatus, such as the terminal apparatus 7, and receive electric power supplied from the external apparatus.

Configuration of Optical Sensor Unit

The optical sensor unit 3 includes an optical filter device 4, which is so configured that a wavelength tunable interference filter 5 is accommodated in an enclosure 40, a telecentric optical system 31, which guides the light under measurement to the wavelength tunable interference filter 5, an imaging device 32, which receives light having passed through the wavelength tunable interference filter 5, and a voltage controller 33, which changes the wavelength of the light allowed to pass through the wavelength tunable interference filter 5.

The optical filter device 4, the telecentric optical system 31, and the imaging device 32 are disposed in predetermined positions in an optical part enclosure 34, both ends of which are open. The imaging device 32 is disposed at the end of the optical part enclosure 34 on the side where the circuit substrate 6 is present, and optical parts that form the telecentric optical system 31 are disposed at the opposite end of the optical part enclosure 34. The opposite end is connected to the light incident port 241 formed in the exterior case 24.

Configuration of Wavelength Tunable Interference Filter

Figure 3:
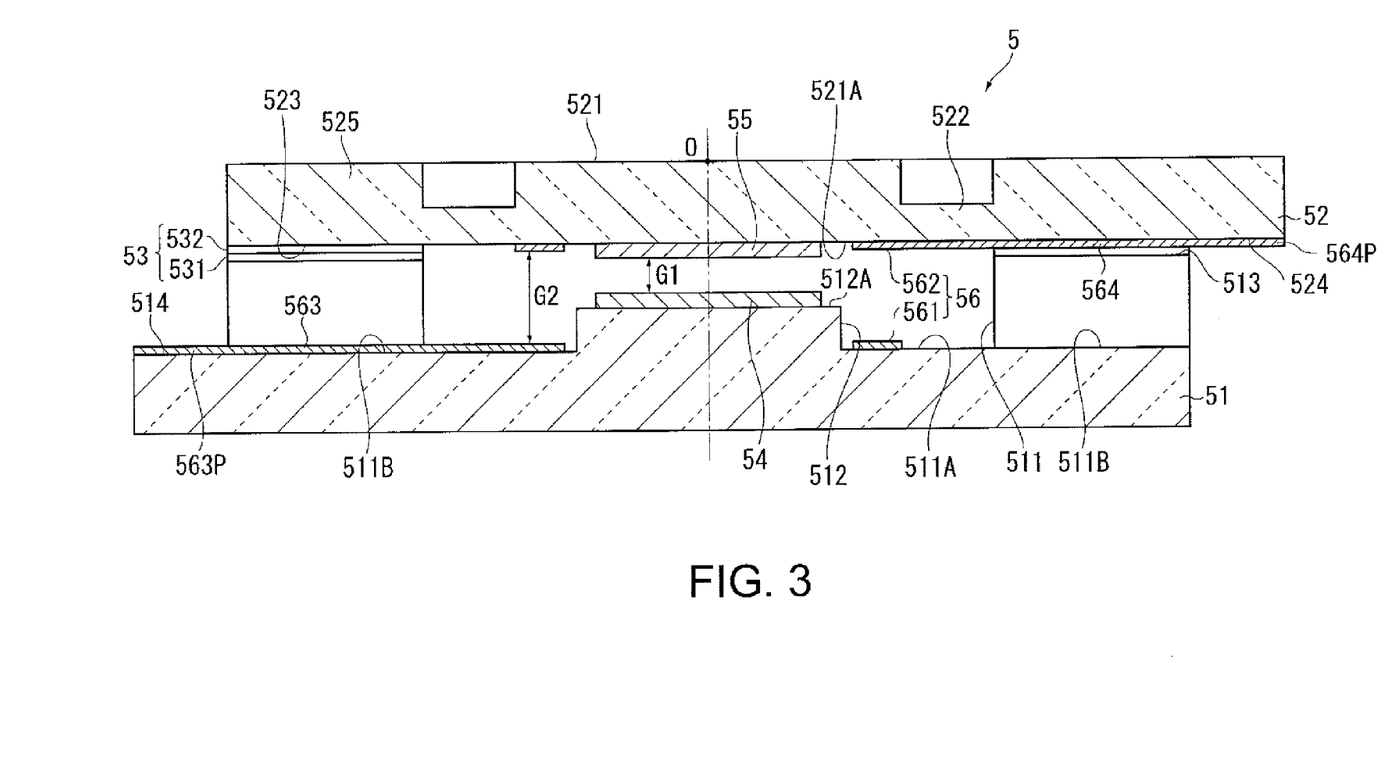
FIG. 3 is a cross-sectional view showing a schematic configuration of a wavelength tunable interference filter.

FIG. 3 is a cross-sectional view showing a schematic configuration of the wavelength tunable interference filter 5.

The wavelength tunable interference filter 5 is accommodated in the enclosure 40, the interior of which is a sealed space and forms a vacuum environment (or an environment in which the pressure is lower than the atmospheric pressure). The wavelength tunable interference filter 5 includes a fixed substrate 51, which is a first substrate according to an embodiment of the invention, and a movable substrate 52, which is a second substrate according to an embodiment of the invention, as shown in FIG. 3. A first bonding portion 513 of the fixed substrate 51 and a second bonding portion 523 of the movable substrate are bonded to each other via a bonding film 53 (first bonding film 531 and second bonding film 532) formed, for example, of a plasma polymerization film primarily made, for example, of siloxane so that the fixed substrate 51 and the movable substrate 52 are integrated with each other.

In the following description, a plan view viewed in the substrate thickness direction of the fixed substrate 51 or the movable substrate 52, that is, a plan view in which the wavelength tunable interference filter 5 is viewed in the direction in which the fixed substrate 51, the bonding film 53, and the movable substrate 52 are stacked on each other is referred to as a filter plan view.

In the filter plan view, one side of the fixed substrate 51 protrudes outward beyond the movable substrate 52. Part of the protruding portion, specifically, the surface visible when the wavelength tunable interference filter 5 is viewed from the side where the movable substrate 52 is present forms a first electric component surface 514.

Further, in the filter plan view, one of the sides of the movable substrate 52, specifically, a side facing away from the first electric component surface 514 protrudes outward beyond the fixed substrate 51. Part of the protruding portion, specifically, the surface visible when the wavelength tunable interference filter 5 is viewed from the side where the fixed substrate 51 is present forms a second electric component surface 524.

The fixed substrate 51 has an electrode placement groove 511 and a reflection film attachment portion 512. The fixed substrate 51 is formed to be thicker than the movable substrate 52 and is not hence bent due to an electrostatic attractive force produced when a voltage is applied between a fixed electrode 561 and a movable electrode 562 or internal stress induced in the fixed electrode 561.

The electrode placement groove 511 is so formed that it has an annular shape around a center point O of the wavelength tunable interference filter 5 in the filter plan view. The reflection film attachment portion 512 is so formed that it protrudes from a central portion of the electrode placement groove 511 in the plan view described above toward the movable substrate 52. A groove bottom surface of the electrode placement groove 511 forms an electrode attachment surface 511A, on which the fixed electrode 561 is disposed. Further, the front end surface of the thus protruding reflection film attachment portion 512 forms a reflection film attachment surface 512A, on which a fixed reflection film 54 is disposed.

The fixed substrate 51 is further provided with an electrode drawing groove 511B, which extends from the electrode placement groove 511 toward the first electric component surface 514 and the second electric component surface 524.

The fixed electrode 561 is disposed on the electrode attachment surface 511A of the electrode placement groove 511. The fixed electrode 561 is specifically disposed on the electrode attachment surface 511A in an area facing the movable electrode 562 on a movable portion 521, which will be described later.

A fixed drawn electrode 563 is provided on the fixed substrate 51 and extends from the outer circumferential edge of the fixed electrode 561 along the electrode drawing groove 511B, which has an annular shape, to the first electric component surface 514. The tip of the thus extending fixed drawn electrode 563 forms a fixed electrode pad 563P on the first electric component surface 514.

The present embodiment relates to a configuration in which the single fixed electrode 561 is provided on the electrode attachment surface 511A but may instead, for example, relate to a configuration in which two concentric electrodes formed around the plan view center point O are provided (dual electrode configuration).

Part of the surface of the fixed substrate 51 that faces the movable substrate 52, specifically, the surface where the electrode placement groove 511, the reflection film attachment portion 512, or the electrode drawing groove 5113 is not formed forms the first bonding portion 513. The first bonding film 531 is disposed on the first bonding portion 513, and the first bonding film 531 is bonded to the second bonding film 532 disposed on the movable substrate 52 so that the fixed substrate 51 and the movable substrate 52 are bonded to each other as described above.

The movable substrate 52 has a circular movable portion 521, which is formed around the plan view center point O, a holding portion 522, which is provided in an area outside the movable portion 521 and holds the movable portion 521, and a substrate outer circumferential portion 525, which is provided in an area outside the holding portion 522, in the filter plan view.

The movable portion 521 is formed to be thicker than the holding portion 522. The movable portion 521 is so formed that it has a diameter greater than at least the diameter of the outer circumferential edge of the reflection film attachment surface 512A in the filter plan view. The movable portion 521 is provided with the movable electrode 562 and a movable reflection film 55, which is a second reflection film according to an embodiment of the invention.

The movable electrode 562 faces the fixed electrode 561 via an inter-electrode gap G2 and has the same annular shape as that of the fixed electrode 561. The movable substrate 52 is further provided with a movable drawn electrode 564, which extends from the outer circumferential edge of the movable electrode 562 toward the second electric component surface 524. The tip of the thus extending movable drawn electrode 564 forms a movable electrode pad 564P on the second electric component surface 524.

The movable reflection film 55 is so disposed on a central portion of a movable surface 521A of the movable portion 521 that the movable reflection film 55 faces the fixed reflection film 54 via an inter-reflection-film gap G1.

The holding portion 522 is a diaphragm that surrounds the movable portion 521 and is formed to be thinner than the movable portion 521. The thus configured holding portion 522 is more readily bent than the movable portion 521 and can hence displace the movable portion 521 toward the fixed substrate 51 in response to a small amount of electrostatic attractive force.

The substrate outer circumferential portion 525 is disposed in an area outside the holding portion 522 in the filter plan view, as described above. The surface of the substrate outer circumferential portion 525 that faces the fixed substrate 51 forms the second bonding portion 523, which faces the first bonding portion 513. The second bonding film 532 is disposed on the second bonding portion 523, and the second bonding film 532 is bonded to the first bonding film 531 so that the fixed substrate 51 and the movable substrate 52 are bonded to each other as described above.

Configurations of Telecentric Optical System, Imaging Device, and Voltage Controller The telecentric optical system 31 is an optical system that guides light incident thereon to the wavelength tunable interference filter 5 and is formed of a plurality of lenses and other optical parts. The telecentric optical system 31 is so configured that the principal ray of the incident light exits out of the telecentric optical system 31 in parallel to the optical axis thereof and perpendicularly to the fixed substrate 51 of the wavelength tunable interference filter 5.

The imaging device 32 is so disposed on the circuit substrate 6 that the imaging device 32 is located in the focal plane of the telecentric optical system 31. The light under measurement originated from the object X under colorimetry is guided through the telecentric optical system 31 and focused on the imaging device 32. The imaging device 32 has a plurality of detection elements (not shown) arranged in the form of an array. Each of the detection elements is formed, for example, of a CCD (charge coupled device), a CMOS device, or any other photoelectric conversion device, produces an electric signal according to the amount of received light, and outputs the electric signal to a light amount acquisition section 63, which will be described later.

The voltage controller 33 applies a drive voltage corresponding to the wavelength of the light allowed to pass through the wavelength tunable interference filter 5 (measured wavelength) under the control of a filter controller 62, which will be described later.

Configuration of Circuit Substrate

The circuit substrate 6 is provided with a variety of controllers for controlling the measurement apparatus 2. Specifically, the circuit substrate 6 is provided with a storage section 61, a filter controller 62, a light amount acquisition section 63, and a light source controller 64, as shown in FIG. 1. The variety of controllers provided on the circuit substrate 6 are achieved by combining computing circuits, memories, a variety of electrical circuits, and other components as appropriate.

The storage section 61 stores a variety of programs and data for controlling the measurement apparatus 2. The data are formed of correlation data or V-λ data showing the drive voltage applied to an electrostatic actuator 56 versus the wavelength of the transmitted light, information on the measured wavelength for measurement of the object x under colorimetry (such as measurement start wavelength, intervals at which wavelength is changed, and measurement end wavelength), and other types of information. The storage section 61 further stores the amounts of received light acquired by the light amount acquisition section 63 as a spectroscopic image having the amounts of received light related to the pixel positions (coordinates) of the detection elements and the measured wavelength at the time of detection.

The filter controller 62 acquires the voltage value of the drive voltage (input value) corresponding to the measured wavelength based on the V-λ data stored in the storage section 61 and outputs the acquired voltage value to the voltage controller 33, which changes the size of the gap in the wavelength tunable interference filter 5.

The filter controller 62 further judges or otherwise processes the following actions: detection of timing at which the measured wavelength is changed; change of the measured wavelength; change of the drive voltage in accordance with the change in the measured wavelength; termination of the measurement based on the variety of data stored in the storage section and controls the voltage controller 33 based on judgment results.

The light amount acquisition section 63 acquires a spectroscopic image by acquiring the amount of transmitted light received with the imaging device 32 on a detection element basis. The spectroscopic image in which the pixel position and the amount of received light are related to each other is further related to the measured wavelength at the time of detection and stored in the storage section 61. The imaging device 32 and the light amount acquisition section 63 correspond to the imaging section according to an embodiment of the invention.

The light source controller 64 controls the light source 21 to start and stop emitting light in accordance with an instruction from the user.

Configuration of Terminal Apparatus

The terminal apparatus 7 includes the display section 71, an input section 72, a communication section 73, and a control unit 74, which controls the terminal apparatus 7, as shown in FIG. 1.

The display section 71 is a liquid crystal display, an organic EL display, or any of other various display devices.

The input section 72 inputs an operation instruction from the user to the control unit 74. Examples of the input section 72 may include a touch panel, a mouse, a keyboard, and any of other various input devices that can detect operation performed on the surface of the display section 71 by the user based on a variety of methods, such as an infrared method, a capacitance method, and an electromagnetic induction method.

The communication section 73 communicates with the measurement apparatus 2 and other external apparatus. The communication section 73 can communicate with them based on wired communication via a LAN or any other network and a variety of types of wireless communication, such as Wi-Fi, Bluetooth, and infrared communication.

The control unit 74 includes a variety of controllers for controlling the terminal apparatus 7 and the colorimetry system 1, specifically, a display controller 741, a specified position detection section 742, a colorimetry section 743, and a colorimetry result output section 744, as shown in FIG. 1. The variety of controllers provided in the control unit 74 are achieved by combining computing circuits, memories, a variety of electrical circuits, and other components as appropriate.

The display controller 741 controls contents displayed on the display section 71. Examples of the displayed contents include not only realtime images captured by the measurement apparatus 2 but also, for example, an operation screen that allows the user to operate the colorimetry system 1 and notification images that notify the user of the action state of the measurement apparatus 2, measurement results, and other types of information.

The specified position detection section 742 identifies a colorimetry performed position specified by the user (specified position). Specifically, the user selects a location where the user desires to perform colorimetry, that is, a specified position in realtime images displayed on the display section 71. Based on the user's operation detected by the input section 72 and the realtime images, the position of the pixel in the specified position is identified. The specified position is thus identified.

The specified position in the present embodiment refers to an area containing a plurality of pixels and having a predetermined range containing the position selected by the user with the input section 72. The range of a specified position may be set in advance or may be set in advance by the user.

The colorimetry section 743 acquires a light amount value at each of the pixels in the specified position based on a spectroscopic image acquired by the measurement apparatus 2 for each of a plurality of wavelengths under measurement and calculates an average light amount value, which is the average of the light amount values at the pixels. The colorimetry section 743 relates the average light amount value in the specified position for each of the wavelengths under measurement to the wavelength under measurement, produces a colorimetry result, and stores the result in a storage section (not shown).

The colorimetry result output section 744 outputs the stored colorimetry result.

Action of Colorimetry System

Figure 4:
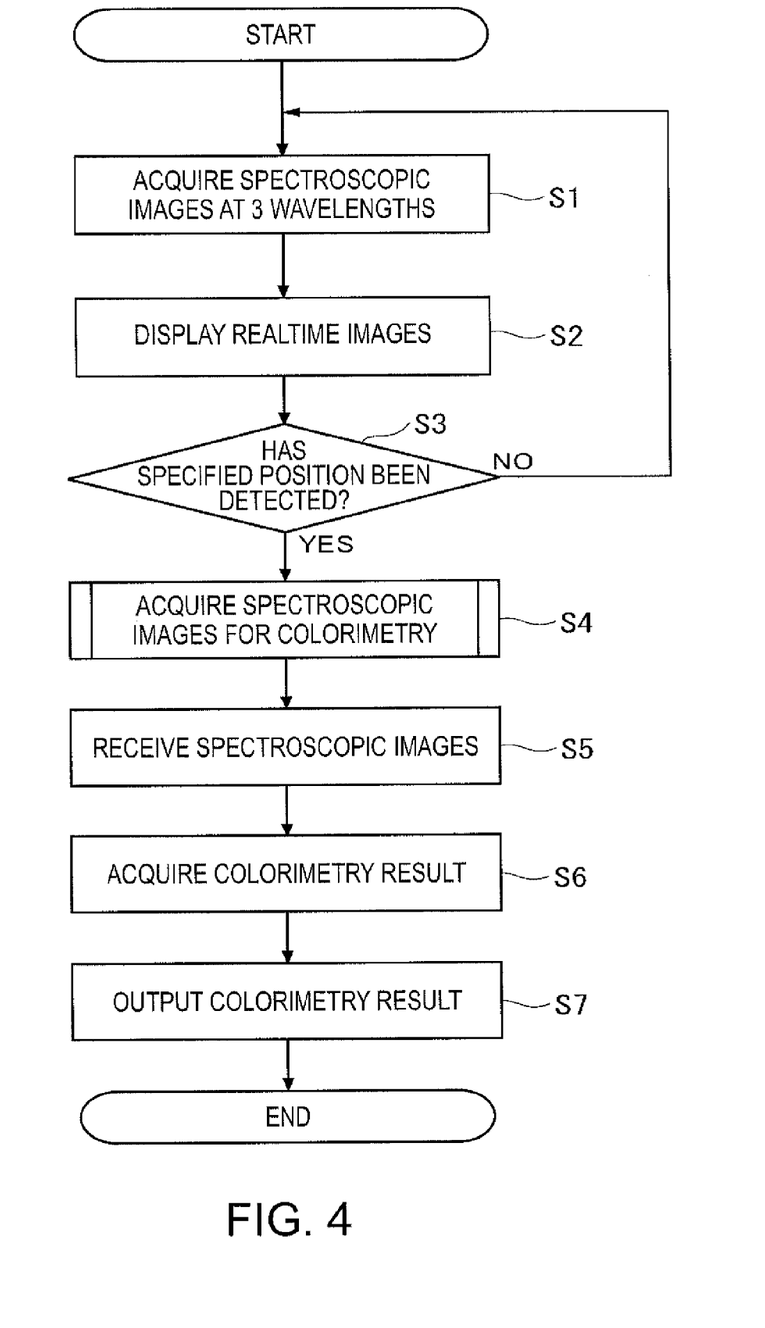
FIG. 4 is a flowchart showing processes carried out by the colorimetry system.

FIG. 4 is a flowchart showing the action of the colorimetry system 1.

To perform colorimetry, the user powers on the measurement apparatus 2 and activates an application program for controlling the colorimetry system 1 that has been installed in advance in the terminal apparatus 7, as shown in FIG. 4. When the application program is activated, the terminal apparatus 7 starts communicating with the measurement apparatus 2 and instructs the measurement apparatus 2 to acquire 3-band realtime images.

Having received the realtime image acquisition instruction, the measurement apparatus 2 acquires 3-band realtime images (step S1). Specifically, spectroscopic images (spectroscopic images for producing combined image) are acquired at predetermined wavelengths set in advance within the following wavelength ranges: R (610 to 760 nm, for example); G (500 to 560 nm, for example); and B (435 to 480 nm, for example), that is, three predetermined wavelengths (3 bands) corresponding to R, G, and B. To this end, the filter controller 62 controls the voltage controller 33 to successively apply drive voltages corresponding to the three predetermined wavelengths to the electrostatic actuator 56. As a result, light fluxes of the three predetermined wavelengths successively pass through the wavelength tunable interference filter 5 and are detected (captured) with the imaging device 32. Spectroscopic images corresponding to the wavelengths are thus successively acquired.

The measurement apparatus 2 successively sends the acquired spectroscopic images for producing a combined image to the terminal apparatus 7. Having received the spectroscopic images for producing a combined image, the terminal apparatus 7 uses the display controller 741 to combine the spectroscopic images for producing a combined image (spectroscopic images corresponding to R, G, and B). The terminal apparatus 7 uses the display section 71 to enlarge and display the combined image as a realtime image of an image capturable area Art (step S2).

Figure 5:
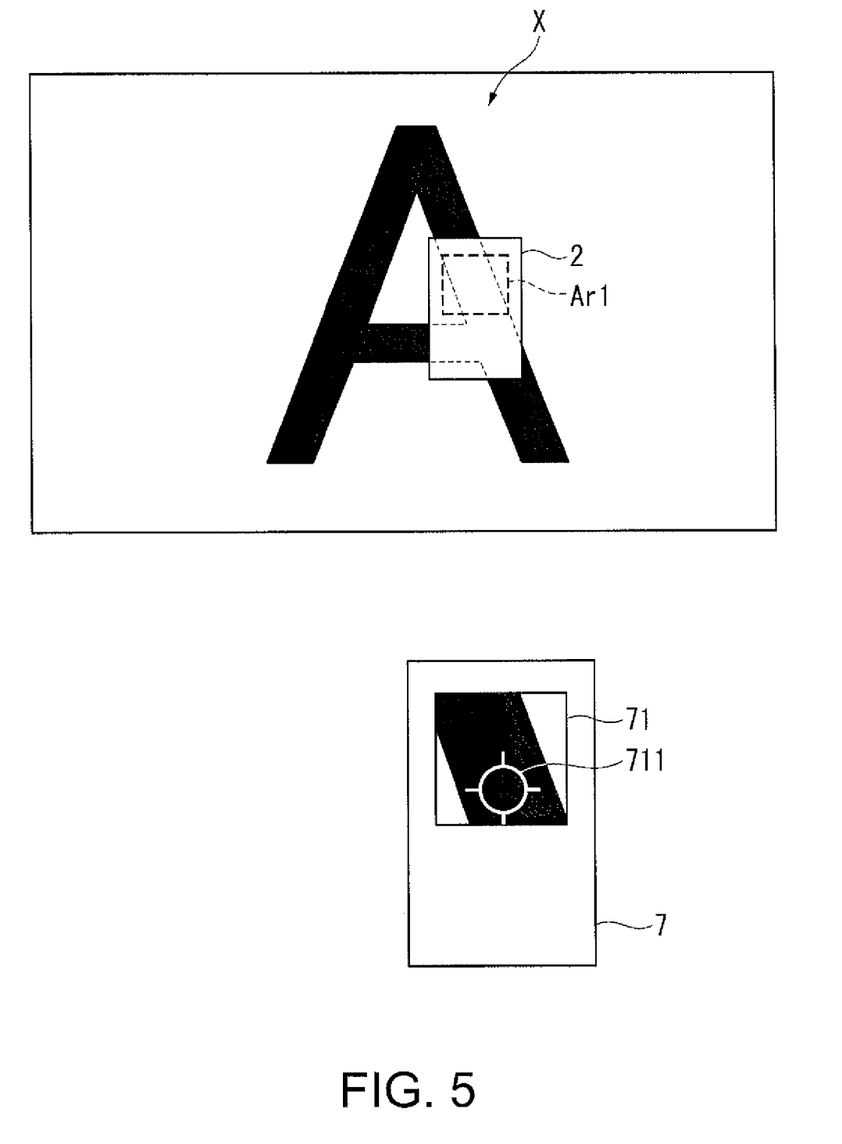
FIG. 5 is a schematic view for describing one of the processes carried out by the colorimetry system.

FIG. 5 shows the measurement apparatus 2 placed on the object X under colorimetry and an example of the realtime images displayed on the display section 71 of the terminal apparatus 7.

When the measurement apparatus 2 is placed on a surface of the object X under calorimetry, an image of the surface covered with the image capturable area Ar1 (area indicated by dotted line in FIG. 5) of the imaging device 32 in the optical sensor unit 3 is captured, as shown in FIG. 5. Realtime images corresponding to the image capturable area Ar1 are therefore displayed on the display section 71 of the terminal apparatus 7.

The user performs predetermined operation of specifying a position where colorimetry is performed (specified position) while looking at the displayed realtime images. The predetermined operation may be operation that can be detected by the input section 72 and taken as operation corresponding to a specified position instruction and a colorimetry start instruction.

The specified position detection section 742 detects an area of the predetermined size containing the user operated position specified by the operation performed on the input section 72 (colorimetry area Ar2) as the specified position (step S3).

Figure 6:
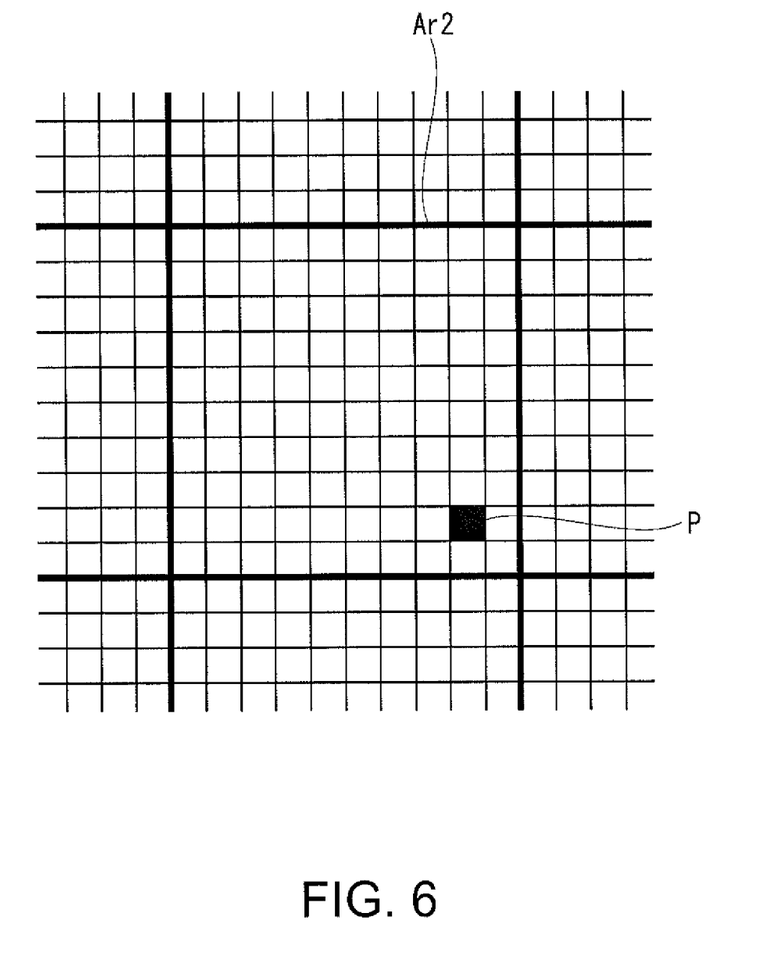
FIG. 6 diagrammatically shows a colorimetry area in the embodiment.

FIG. 6 diagrammatically shows an example of the specified position in the present embodiment. A captured spectroscopic image is divided in advance into pixel areas each formed, for example, of 10×10 pixels, and the specified position detection section 742 detects a pixel area containing a pixel P corresponding to the user operated position specified by the input operation as the colorimetry area Ar2, as shown in FIG. 6.

When the user specifies the colorimetry performed position, a cursor 711 indicating the specified position may be displayed on the display section 71, as shown in FIG. 5.

The colorimetry system 1 keeps acquiring and displaying realtime images until the user specifies a colorimetry performed position.

Having detected the specified position, the terminal apparatus 7 sends information on the positions of the pixels in the specified position (hereinafter referred to as specified position information) to the measurement apparatus 2 and instructs the measurement apparatus 2 to start colorimetry processes. Having received the specified position information and the colorimetry start instruction from the terminal apparatus 7, the measurement apparatus 2 acquires spectroscopic images for colorimetry (step S4).

Acquisition of Spectroscopic Images for Colorimetry

Figure 7:
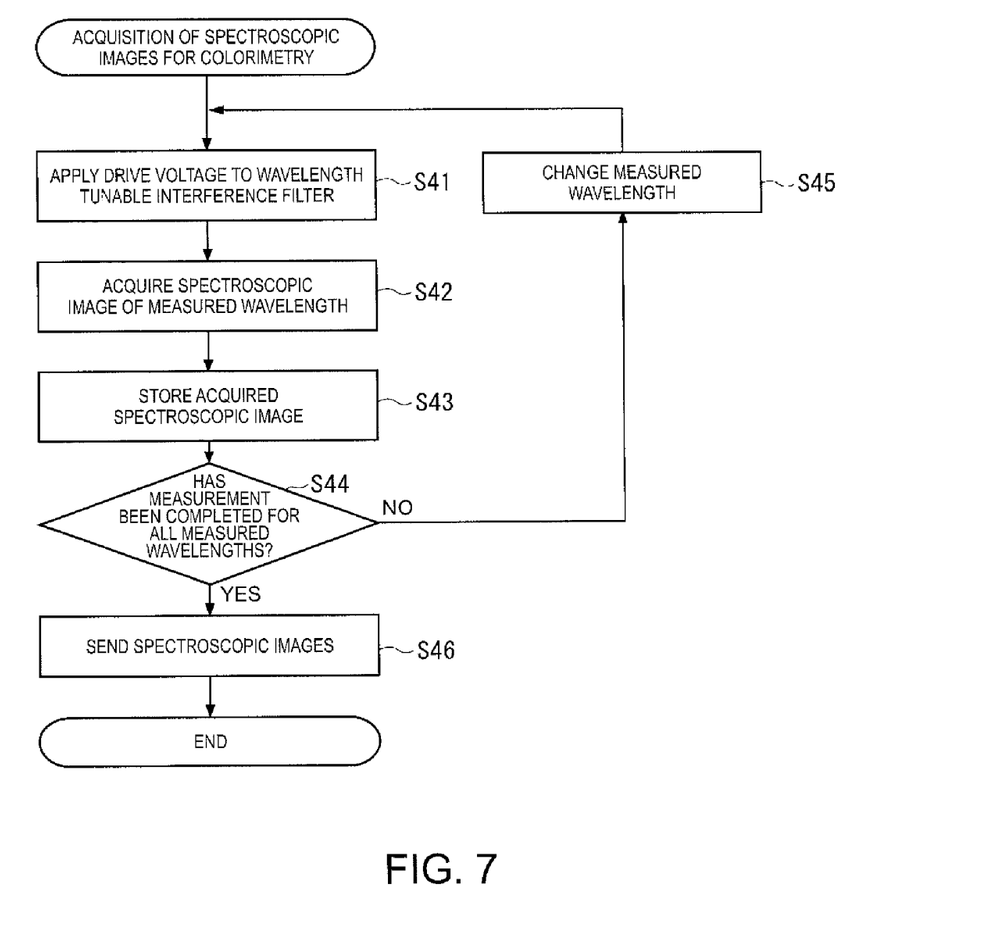
FIG. 7 is a flowchart showing a colorimetry process shown in FIG. 4.

FIG. 7 is a flowchart showing details of the process of acquiring spectroscopic images for colorimetry in step S4 shown in FIG. 4.

Having received the colorimetry start instruction, the measurement apparatus 2 acquires a spectroscopic image for colorimetry corresponding to each of the plurality of measured wavelengths.

First, the filter controller 62 controls the voltage controller 33 to apply a drive voltage corresponding to one of the preset measured wavelengths to the electrostatic actuator 56 in the wavelength tunable interference filter 5 (step S41), as shown in FIG. 7.

When the drive voltage described above is applied to the electrostatic actuator 56, the inter-reflection-film gap G1 is changed to a dimension according to the drive voltage. Light of the measured wavelength then passes through the wavelength tunable interference filter 5 and is detected with the imaging device 32, and the light amount acquisition section 63 acquires light amount values to acquire a spectroscopic image for colorimetry (step S42). In this process, the light amount acquisition section 63 acquires only the light amount values at the pixels corresponding to the colorimetry area Ar2 based on the specified position information. A spectroscopic image of only an area corresponding to the colorimetry area Ar2 is thus acquired.

The acquired spectroscopic image is stored in the storage section 61 with the amount of received light, the pixel position, and the measured wavelength related to one another (step S43).

The filter controller 62 then judges whether or not spectroscopic images of the displayed object X under colorimetry have been acquired by performing the measurement at all the preset measured wavelengths, that is, whether or not the measurement has been completed for all the measured wavelengths (step S44). When the measurement has not been completed for all the measured wavelengths, the filter controller 62 changes the measured wavelength (step 945). Steps S41 to S45 are then repeated until the measurement is completed for all the measured wavelengths.

When the measurement has been completed for all the measured wavelengths, the measurement apparatus 2 sends the spectroscopic images of the measured wavelength stored in the storage section 61 to the terminal apparatus 7 (step S46). The spectroscopic images may alternatively be sent whenever a spectroscopic image is acquired at each of the measured wavelengths.

Referring back to FIG. 4, when the terminal apparatus 7 receives the spectroscopic images of the measured wavelengths from the measurement apparatus 2 (step S5), the colorimetry section 743 uses the spectroscopic images in the specified position (colorimetry area Art) to acquire a colorimetry result (step S6).

Specifically, the colorimetry section 743 calculates the average of the light amount values at all the pixels in each of the spectroscopic images captured in the specified position (colorimetry area Ar2). Spectral data in which the average light amount value calculated for the spectroscopic image of each of the measured wavelengths is related to the corresponding measured wavelength are acquired as a colorimetry result and stored in the storage section (not shown), such as a memory, in the control unit 74.

The colorimetry result output section 744 then outputs the colorimetry result measured in step S6 (step S7). The output of the colorimetry result may, for example, be displayed on the display section 71 or may be sent to a printer, an image display apparatus, or any other external apparatus as required.

Advantageous Effects of Embodiment

In the colorimetry system 1, the measurement apparatus 2 captures light under measurement from the object X under colorimetry at three bands to produce realtime images and displays them on the display section 71 of the terminal apparatus 7. When the user specifies a position where the user desires to perform colorimetry in the image displayed on the terminal apparatus 7, the specified position detection section 742 detects the specified position where the colorimetry is performed based on the user's operation.

Further, when the specified position is detected, the measurement apparatus 2 causes the wavelength tunable interference filter 5 to transmit light fluxes of a plurality of wavelengths for colorimetry sequentially from the light under measurement and captures a spectroscopic image for colorimetry corresponding to each of the wavelengths. The terminal apparatus 7 then measures light amount values of each of the spectroscopic images for colorimetry in the specified position for each of the wavelengths and outputs the measured values as a colorimetry result.

As described above, the user selects a specified position while looking at displayed realtime images. Therefore, to select a specified position, spectroscopic images for producing realtime images are acquired, and to perform colorimetry, spectroscopic images for colorimetry are acquired. It is therefore necessary to acquire no spectroscopic image for colorimetry in an area where no colorimetry is performed or spectroscopic images can be acquired only in an area where colorimetry is performed, whereby accurate colorimetry can be efficiently performed on an arbitrary object X under colorimetry.

Further, the colorimetry system 1 first detects a specified position (step S3) and then acquires each spectroscopic image for colorimetry (step S4). As a result, an area corresponding to the specified position on the object X under colorimetry can be identified, and an area over which spectroscopic images are acquired can be so limited that the area contains the area corresponding to the specified position on the object X under calorimetry. Therefore, no spectroscopic image for colorimetry is acquired in an area where colorimetry is not performed but spectroscopic images for colorimetry can be acquired only in an area where colorimetry is performed, whereby the time required for the acquisition of spectroscopic images for colorimetry can be shortened and hence the color of the object X under colorimetry can be efficiently measured.

In particular, in the present embodiment, each acquired spectroscopic image for colorimetry is an image formed of pixels contained in a portion specified as a specified position.

As a result, spectroscopic images for colorimetry can be acquired only in a minimum area containing the specified position and hence the time required for the acquisition of spectroscopic images for colorimetry can further be shortened, whereby the color of the object X under colorimetry can be more efficiently measured.

Further, in the colorimetry system 1, which acquires a spectroscopic image corresponding to each of the three wavelengths as images for producing a realtime image (combined image), combines the acquired spectroscopic images, and displays the combined image as a realtime image on the display section 71, the user can make the selection while looking at the captured realtime image of the object X under colorimetry. The user can therefore appropriately and readily select a desired position on an object under colorimetry as the specified position and acquire a desired colorimetry result. In particular, even when the user has not determined a position where the user desires to perform colorimetry and is moving the measurement apparatus 2 over the object X under colorimetry, the colorimetry is performed in the present embodiment after the position where the user desires to perform colorimetry is determined, whereby power consumption involved in the colorimetry can be reduced.

In the colorimetry system 1, spectroscopic images for producing realtime images (combined images) are acquired at each of the three wavelengths corresponding to R, G, and B. As a result, an image that is equivalent or similar to the object X under colorimetry can be displayed as a realtime image. The user can therefore readily identify a position corresponding to a position on the object X under colorimetry where the user desires to perform colorimetry based on the realtime images displayed on the display section 71, whereby the user can more appropriately and readily select a desired position as the specified position.

In the colorimetry system 1, enlarged images of part of the object X under colorimetry are displayed on the display section 71 of the terminal apparatus 7. The user can therefore specify a specified position while looking at the enlarged, displayed realtime images of the object X under colorimetry, whereby the user can more appropriately and readily select a desired position as the specified position.

In the colorimetry system 1, the wavelength tunable interference filter 5 is used as a spectroscopic filter capable of performing two-dimensional spectroscopy. As a result, the time required for colorimetry can be shortened and realtime images can be preferably acquired. Further, a Fabry-Perot etalon can be smaller, for example, than an AOTF and an LCTF, whereby the size of the measurement apparatus can be reduced.

In the colorimetry system 1, a specified position is the colorimetry area Ar2 containing a plurality of pixels, and the colorimetry result output section 744 outputs a colorimetry result or the average of light amount values over a specified area in each spectroscopic image for colorimetry as the light amount value in the specified position.

As a result, variation in the color of the object x under colorimetry between dots (pixels) in the colorimetry area Ar2 and variation in light reception sensitivity between the pixels of the imaging device 32 can be averaged, whereby the S/N ratio of a colorimetry result can be improved.

The colorimetry system 1 includes the light blocker 25, which is disposed around the light incident port 241, through which light from the object X under colorimetry is introduced, to block external light other than the light from the object under colorimetry.

The thus configured light blocker comes into contact with a surface of the object under colorimetry and can prevent external light other than the light from the object X under colorimetry from entering the system, whereby the colorimetry can be performed more accurately.

The light blocker 25 preferably has an anti-reflective, light blocking surface. In this case, light will not be reflected off the surface, whereby no reflected light affects the calorimetry and no external light other than the light from the object under colorimetry will enter the system.

Variations of Embodiment

The invention is not limited to the embodiment described above, and variations, improvements, and other modifications to the extent that they still achieve the advantage of the invention fall within the scope of the invention.

For example, in the embodiment described above, to detect a specified position, a spectroscopic image is divided in advance, for example, into 10×10 pixel areas, and the pixel area containing the pixel P corresponding to a user operated position (colorimetry area Ar2) is detected as the specified position, as shown in FIG. 6, but the invention is not necessarily configured this way.

Figure 8:
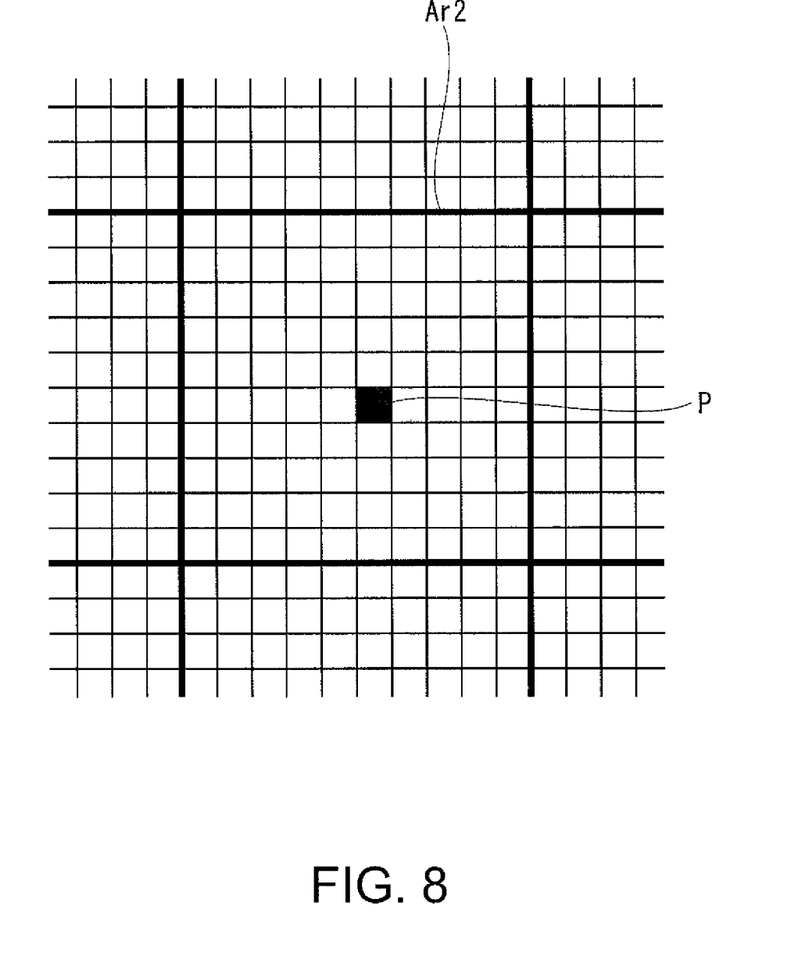
FIG. 8 diagrammatically shows another example of the colorimetry area.

FIG. 8 diagrammatically shows another example of the colorimetry area Ar2. The specified position detection section 742 may detect a specified position by setting the colorimetry area Ar2 in such a way that the pixel P corresponding to the user operated position is located, for example, at the center (central 2×2 pixel area) of a 10×10 pixel area, as shown in FIG. 8. The colorimetry area Ar2 around the pixel P corresponding to the user operated position can thus be set.

In the embodiment described above, to acquire spectroscopic images for colorimetry, the light amount acquisition section 63 acquires the amount of light incident only on a pixel area corresponding to the colorimetry area Ar2 to acquire a spectroscopic image of the area, but the invention is not necessarily configured this way.

That is, the light amount acquisition section 63 may acquire a spectroscopic image by acquiring the amount of light incident on pixels including those of the imaging device 32 other than those in the pixel area corresponding to the colorimetry area Ar2, for example, all pixels in the image capturable area Ar1 of the imaging device 32. In this case, the terminal apparatus 7, when it calculates spectral data, acquires the amount of light incident on the pixels corresponding to a specified position (colorimetry area Ar2) in the spectroscopic image.

In the embodiment described above, a specified position has a preset range containing the pixel P corresponding to a user operated position (pixel area formed of 10×10 pixels, for example), but the invention is not necessarily configured this way.

For example, the specified position detection section 742 detects the colorimetry area Ar2 containing the pixel P as in the embodiment described above, then may process each spectroscopic image for producing a combined image as a realtime image or a combined image that is a combination of the spectroscopic images to calculate the spectrum in each coordinate position in the image in the colorimetry area Ar2, and judge whether or not a pixel of a color different from that of the pixel P is contained in the image in the colorimetry area Ar2. When a pixel of a different color is contained in the image in the colorimetry area Ar2, the specified position detection section 742 may identify a specified position by setting a new colorimetry area Ar2 produced by reducing the current colorimetry area Ar2 in such a way that the pixel is excluded from the new colorimetry area Ar2.

Colorimetry can be performed more accurately by setting the colorimetry area Ar2 (specified position) in such a way that it does not contain a pixel that receives light of a different color as described above. Further, the user can readily perform accurate colorimetry without having to manually change the colorimetry range.

It is noted that the specified position may instead be formed of only the single pixel P.

In the embodiment described above, the colorimetry system 1 including the measurement apparatus 2 and the terminal apparatus 7, which can communicate with each other, has been described as an example of the colorimetry apparatus according to the embodiment of the invention, but the invention is not necessarily configured this way. That is, the colorimetry apparatus according to the embodiment of the invention may not necessarily be formed of the measurement apparatus 2 and terminal apparatus 7 separate from each other but may be formed of a single apparatus.

In the embodiment described above, to acquire realtime images, spectroscopic images are acquired at three wavelengths corresponding to R, G, and B, but the invention is not necessarily configured this way. That is, spectroscopic images may be acquired at three or more wavelengths.

In the embodiment described above, realtime images enlarged as compared with the object X under colorimetry are displayed on the display section 71, but realtime images are not necessarily enlarged before displayed and may be displayed in actual size. Further, the enlargement factor may be changeable.

In the embodiment described above, the colorimetry section 743 produces a colorimetry result in the form of spectral data on a spectroscopic image for colorimetry in the colorimetry area Art, but the invention is not necessarily configured this way. That is, a colorimetry result of a spectroscopic image for colorimetry may be produced on a pixel basis. In this case, even when the user changes a specified position to another, a colorimetry result can immediately be outputted.

In the embodiment described above, the wavelength tunable interference filter 5 is used as the spectroscopic filter, but the invention is not necessarily configured this way. For example, a spectroscopic filter capable of two-dimensional spectroscopy, such as a liquid crystal tunable filter and an AOTF, may be used.

In the embodiment described above, the wavelength tunable interference filter 5 is so configured by way of example that the fixed reflection film 54, which is a first reflection film, is provided on the fixed substrate 51, which is the first substrate, and the movable reflection film 55, which is a second reflection film, is provided on the movable substrate 52, which is the second substrate, but the invention is not necessarily configured this way. For example, the first substrate and the second substrate may be omitted. In this case, for example, after the first reflection film is provided on one surface of a parallel glass substrate, and the second reflection film is provided on the other surface, which is parallel to the one surface, the parallel glass substrate is etched, for example, in an etching process. In this configuration, in which 110 first or second substrate is provided, the thickness of the spectroscopic device can be further reduced. In this case, the dimension of the gap between the reflection films can be maintained by providing a spacer or any other component interposed between the first reflection film and the second reflection film. Further, the dimension of the gap between the reflection films can be changed by providing a first electrode on the first reflection film and a second electrode on the second reflection film and applying a drive voltage between the first electrode and the second electrode.

In the embodiment described above, the light source 21 is provided, but the light source 21 is not necessarily provided when the object X under colorimetry is limited to any of those displayed on a variety of self-luminous displays.

In the embodiment described above, the telecentric optical system 31 is provided, but the invention is not necessarily configured this way. A light guide system capable of guiding light from an object under colorimetry to the spectroscopic filter only needs to be provided. For example, an LCF may instead be provided.

In the embodiment described above, the light blocker 25 is formed of an elastic member, but the invention is not necessarily configured this way. That is, the light blocker 25 may be formed of a hard member that does not elastically deform. When the thus configured light blocker 25 is pressed against the object X under colorimetry, the measurement apparatus 2 is readily fixed to printed matter because the light blocker 25 does not deform. Therefore, when a surface of the light blocker 25 that comes into contact with printed matter or any other object is so configured that the measurement apparatus 2 is inclined to the printed matter or any other object by a desired relative angle (for example, the contact surface is perpendicular to the optical axis of the telecentric optical system 31), the relative angle is readily maintained within an acceptable desired or relative angular range, whereby colorimetry can be performed with improved accuracy.

In addition to the above variations, the specific structure according to the embodiment of the invention can be an appropriate combination of the embodiment and the variations described above or changed as appropriate to any other structure in actual implementation of the invention to the extent that the advantage of the invention is achieved.

The entire disclosure of Japanese Patent Application No. 2013-020167 filed on Feb. 5, 2013 is expressly incorporated by reference herein.

What is claimed is:

1. A colorimetry apparatus comprising:
   a spectroscopic filter;
   a detector that detects light from the spectroscopic filter;
   a controller that acquires a combined image that is a combination of a plurality of images, the plurality of images including a first image of a first wavelength and a second image of a second wavelength,
   wherein the controller specifies a specified position in the combined image; and
   a colorimeter that acquires color of the specified position, wherein
   the specified position include a first position and a second position, and the colorimeter acquire color of the first position, and
   the spectroscopic images for colorimetry are acquired after the specified position on the realtime image is detected by the detector.

2. The colorimetry apparatus according to claim 1, further comprising:
   a display that displays the combined image.

3. A colorimetry apparatus comprising:
   a spectroscopic filter capable of separating and selecting incident light;
   a detector that detects light from the spectroscopic filter;
   a display that displays a combined image in real time, the combined image being a realtime image that is a combination of a plurality of images acquired by the detector, the plurality of images including a first image of a first wavelength and a second image of a second wavelength;
   a specified position detector that detects a specified position in the combined image,
   wherein realtime images are continuously acquired and displayed until the specified position is detected; and
   a colorimeter that acquires color of the specified position,
   wherein the spectroscopic images for colorimetry are acquired after the specified position on the realtime image is detected by the detector.

4. The colorimetry apparatus according to claim 3,
   the specified position including a first position and a second position,
   the colorimeter acquiring color of the first position.

5. The colorimetry apparatus according to claim 4, further comprising:
   a controller that specifies the specified position, the controller including the specified position detector.

6. A colorimetry apparatus comprising:
   a spectroscopic filter capable of separating and selecting light of a predetermined wavelength from light incident from an object under colorimetry and changing the wavelength of the light to be selected;
   a detector that detects the amount of light of the wavelength selected by the spectroscopic filter to acquire a spectroscopic image;
   a display;
   a display controller that causes the display to display a combined image in real time, the combined image being a realtime image that is a combination of spectroscopic images of at least three wavelengths acquired by the detector;
   a specified position detector that detects a specified position specified by a user's input operation on the realtime image displayed on the display,
   wherein realtime images are continuously acquired and displayed until the specified position is detected; and
   a colorimeter that measures the color of the object under colorimetry in the specified position based on the amount of light obtained in the specified position, the specified position formed of part of pixels of each of spectroscopic images for colorimetry corresponding to a plurality of wavelengths acquired by the detector, wherein the spectroscopic images for colorimetry are acquired after the specified position on the realtime image is detected by the detector.

7. The colorimetry apparatus according to claim 6, wherein the spectroscopic filter is a wavelength tunable Fabry-Perot etalon.

8. The colorimetry apparatus according to claim 6, wherein the specified position is a specified area containing a plurality of pixels, and the colorimeter measures the color based on the average of the amounts of light obtained in the specified area in each of the spectroscopic images for colorimetry.

9. The colorimetry apparatus according to claim 6, wherein the colorimeter measures the color at each pixel in each of the spectroscopic images for colorimetry.

10. The colorimetry apparatus according to claim 6, further comprising;

a light incident port through which the light incident from the object under colorimetry is introduced; and a light blocker that is disposed around the light incident port and blocks external light other than the light incident from the object under colorimetry.

11. A colorimetry method in a colorimetry apparatus including a spectroscopic filter capable of separating and selecting light of a predetermined wavelength from light incident from an object under colorimetry and changing the wavelength of the light to be selected, a detector that detects the amount of light of the wavelength selected by the spectroscopic filter to acquire a spectroscopic image, a display, a display controller that causes the display to display a combined image that is a combination of spectroscopic images of at least three wavelengths acquired by the detector, a specified position detector that detects a specified position specified by user's input operation in the combined image displayed on the display, and a colorimeter that measures the color of the object under colorimetry in the specified position based on the amount of light obtained in the specified position, the specified position formed of part of pixels of each of spectroscopic images for colorimetry corresponding to a plurality of wavelengths acquired by the detector, the method comprising:

causing the detector to detect the amount of light separated by the spectroscopic filter for the at least three wavelengths to acquire the spectroscopic images for producing the combined image;

causing the display controller to display the combined image in real time, the combined image being a real-time image, which is the combination of the spectroscopic images for producing the combined image, on the display;

causing the specified position detector to detect the specified position specified by the user's input operation on the realtime image displayed on the display;

causing the detector to detect the amount of light separated by the spectroscopic filter for a plurality of wavelengths to acquire the spectroscopic images for colorimetry, wherein realtime images are continuously acquired and displayed until the specified position is detected; and causing the colorimeter to measure the color in the specified position based on the spectroscopic images for colorimetry, wherein the spectroscopic images for colorimetry are acquired after the specified position on the realtime image is detected by the detector.

12. The colorimetry method according to claim 11, wherein acquiring the spectroscopic images for colorimetry is performed for pixels contained in a portion specified as the specified position in detecting the specified position.

* * * * *